United States Patent [19]
de Lacharriere et al.

[11] Patent Number: 5,679,360
[45] Date of Patent: Oct. 21, 1997

[54] SUBSTANCE P ANTAGONIST FOR THE TREATMENT OF LICHENS, PRURIGO, PRURITUS

[75] Inventors: Olivier de Lacharriere, Paris; Lionel Breton, Versailles, both of France

[73] Assignee: L'Oreal, Paris, France

[21] Appl. No.: 574,653

[22] Filed: Dec. 19, 1995

[30] Foreign Application Priority Data

Dec. 19, 1994 [FR] France ................... 94 15251

[51] Int. Cl.$^6$ .................................. A61K 7/48
[52] U.S. Cl. .................. 424/401; 424/434; 424/436; 424/450; 424/489; 514/2; 514/844; 514/937; 514/944
[58] Field of Search .................. 424/401, 434, 424/436, 450, 489; 514/2, 844, 937, 944

[56] References Cited

U.S. PATENT DOCUMENTS

| | | | |
|---|---|---|---|
| 3,772,431 | 11/1973 | Mlkvy et al. | 424/44 |
| 3,888,976 | 6/1975 | Mlkvy et al. | 424/44 |
| 4,477,439 | 10/1984 | D'Alelio | 424/162 |
| 4,943,432 | 7/1990 | Biener | 424/647 |
| 4,980,184 | 12/1990 | Gordon | 424/53 |
| 4,986,981 | 1/1991 | Glace et al. | 424/50 |
| 5,079,010 | 1/1992 | Natterer | 424/617 |
| 5,091,171 | 2/1992 | Yu et al. | 424/642 |
| 5,202,130 | 4/1993 | Grant et al. | 424/671 |

FOREIGN PATENT DOCUMENTS

| | | |
|---|---|---|
| 0 401 503 | 4/1990 | European Pat. Off. . |
| 0 522 808 | 7/1992 | European Pat. Off. . |
| 0586929 | 3/1994 | European Pat. Off. . |
| 2271774 | 4/1994 | United Kingdom . |
| 83/01252 | 4/1983 | WIPO . |
| 87/01935 | 10/1986 | WIPO . |
| 93/01165 | 7/1992 | WIPO . |
| 93/14084 | 7/1993 | WIPO . |
| 96/19184 | 6/1996 | WIPO . |

OTHER PUBLICATIONS

S.M. Moussaoui et al, Br. J. Pharmacol., "A non-peptide NK$_1$-receptor antagonist, RP 67580, inhibits neurogenic inflammation postsynaptically", vol. 109, No. 1, 1993, pp. 259–265.

J. Wallengren, Br. J. Dermatol., "Substance P antagonist inhibits immediate and delayed type cutaneous hypersensitivity reactions", vol. 124, No. 4, 1991, pp. 324–328.

J. Wallengren, et al, Contact Dermatitis, "Some neuropeptides as modulators of experimental contact allergy", vol. 19, No. 5, 1988, pp. 351–354.

T. Lotti et al, J. Am. Acad. Dermatol., "Treatment of aquagenic pruitus with topical capsaicin cream", vol. 30, No. 2PT1, Feb. 1994, pp. 232–235.

T. Sakurada et al, Brain Res., "A selective and extremely potent antagonist of the neurokinin–1 receptor", vol. 593, No. 2, 1992, pp. 319–322.

Rajadhyaksha, Chemical Abstracts, vol. 107, #223281 (1987).

DiSchiena, Chemical Abstracts, vol. 106, #107768 (1987).

Smith et al, Chemical Abstracts, vol. 114, #206554 (1991).

Dufetal et al, Chemical Abstracts, vol. 116, #135998 (1992).

Jancso–Gabor, "Action of rare earth metal complexes on neurogenic as well as on bradykinin–induced inflammation", J. Pharm. Pharmac., 22:366–371 (1970).

Uy Dong Sohn et al, "Agonist–Independent, Muscle-–Type–Specific Signal Transduction Pathways in Cat Esophageal and Lower Esophageal Sphincter Circular Smooth Muscle", J. of Pharmacology & Experimental Therapeutics, 273:481–491 (1995).

Mitsuo Ishizawa, "Contractile Responses of Longitudinal Muscle Strip to 5–HT and Influences of Divalent Cations in the Guinea–Pig Isolated Colon", J. Smooth Muscle Res., 30:65–72 (1994).

H. Goodman, Cosmetic Dermatology, First Edition, Fourth Impression, p. 181 (1936).

Martindale, The Extra Pharmacopoeia, Twenty–seventh Edition, The Pharmaceutical Press, London, pp. 219, 1775 and 1814 (1977).

McGraw–Hill Dictionary of Scientific and Technical Terms, Fifth Edition, pp. 109 and 332.

Sohn et al, "Different Receptors Activate a Different Single G–Protein in Esophageal, (Gis) and in LES (Gq) Circular Smooth Muscle", Gastroenterology, vol. 104 (1993), Abstract.

Maison G. deNavarre, The Chemistry and Manufacture of Cosmetics, 2nd Ed. vol. IV, p1261 (1975).

Alexander A. Fisher, "Irritant Reactions from Topical Urea Preparations Used for Dry Skin Advantages of a Urea–Free 'Dead Sea Salt' Cream", Current Contact News, vol. 18, pp761–772 (1976).

The United States Pharmacopeia, "Alumina/Drug Substances and Dosage Form", pp20 and 22 (1975).

Nordia Briefs, "A Salt–Containing Cream for Dry Skin", No. 484, Jan. 1978.

Cosmetic Counter, vol. 109, Oct. 1994, p. 15.

Primary Examiner—Jyothsan Venkat
Attorney, Agent, or Firm—Burns, Doane, Swecker & Mathis, L.L.P.

[57] ABSTRACT

The invention relates to the use of a substance P antagonist for the preparation of a pharmaceutical composition, in particular for topical application, for treating lichens, prurigo, pruriginous toxicoderma and severe pruritus of neurogenic origin.

19 Claims, No Drawings

SUBSTANCE P ANTAGONIST FOR THE TREATMENT OF LICHENS, PRURIGO, PRURITUS

The present invention relates to the use of a substance P antagonist for the preparation of a pharmaceutical composition for treating certain skin disorders of neurogenic origin.

More especially, this composition permits the treatment, topically, orally or by injection, of lichens, in particular lichen planus and pigmentary lichens; prurigo, and especially actinic prurigo, Besnier's or Hebra's prurigo or strophulus or Hyde's disease; pruriginous toxicoderma and severe pruritus of neurogenic origin, especially those of patients who have undergone haemodialysis and AIDS patients, and cholestatic or biliary pruritus. Pruriginous toxicoderma is, in particular, the outcome of the intake of a medicinal product; these disorders are very different from urticaria, and do not involve any contact reaction.

Hitherto, lichen planus and pigmentary lichens were treated by means of local corticoids or of PUVA therapy. Corticoids are admittedly very effective for calming the symptoms, but unfortunately they display side-effects which are often very detrimental, such as atrophy or infections, especially fungal or bacterial infections. PUVA therapy is the local irradiation of the diseased skin with UVA after absorption of a photosensitizing substance (psoralen). This technique has the serious drawbacks of a light-induced ageing which can, more often than not, give rise to skin cancers. Furthermore, this treatment is not ambulatory, commonly obliging the patients to go to a specialized centre for the entire treatment period, which is very restrictive and limits the exercising of their occupation.

Prurigo is also treated with local corticoids, PUVA therapy or thalidomide. Local corticoids and PUVA therapy have the above drawbacks. Thalidomide has the major drawback of being teratogenic, thereby prohibiting its use in pregnant women. Furthermore, the closely regulated prescription of this drug (limited to hospital doctors) limits its use.

Pruriginous toxicoderma is currently treated by means of local corticoids and/or antihistamines: its treatment hence has the same drawbacks as those mentioned above.

Severe pruritus is also treated with local corticoids, with the same drawbacks as those mentioned above.

The subject of the present invention is, in fact, the use in a pharmaceutically or dermatologically acceptable medium of one or more substance P antagonists enabling certain skin disorders to be treated effectively while remedying the disorders mentioned above.

Substance P is a polypeptide chemical component produced and released by a nerve ending. It belongs to the tachykinin family. Substance P participates, in particular, in the transmission of pain and in central nervous system disorders such as anxiety and schizophrenia, in respiratory and inflammatory disorders, in gastrointestinal disorders, in rheumatic disorders and in certain skin disorders such as eczema, psoriasis, urticaria and contact dermatitis.

It is known to use substance P antagonists to treat these disorders. To this end, reference may be made to the documents U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569, GB-A-2,216,529, EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545, 478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522,808, WO-A-93/01165, WO-A-93/10073 and WO-A-94/08997.

However, nobody had envisaged hitherto treating lichens, prurigo, pruriginous toxicoderma and severe pruritus of neurogenic origin by means of substance P antagonists.

Some of the documents cited above, as well as the documents JP-05-339,240 and JP-06-199,892, describe a large number of disorders which may be treated with compositions containing substance P antagonists, and, among others, some of the skin disorders also known as dermatoses. The invention relates to the symptomatic treatment (itching, irritation) of a dermatosis and not to the treatment of the disorder in itself. Thus, the invention relates to the use of a substance P antagonist for treating the discomfort associated with certain dermatoses, and especially with eczema and with atopic dermatitis, and not to the treatment of the other signs of these dermatoses (vesicles, erythema, and the like).

Moreover, the skin disorders mentioned in these documents are allergies and not disorders of neurogenic origin. Now, the invention does not relate to the treatment of allergies. In effect, allergy is an immunological process which takes place only when an allergen is present and which affects only certain sensitized subjects, whereas disorders of neurogenic origin may affect any individual.

Consequently, the documents mentioned above neither describe nor suggest in any way the use of substance P antagonists for treating symptoms of neurogenic origin.

Hence the subject of the present invention is the use of at least one substance P antagonist for the preparation of a pharmaceutical or dermatological composition for treating lichens, prurigo, pruriginous toxicoderma and severe pruritus of neurogenic origin.

The composition of the invention contains a pharmaceutically or dermatologically acceptable medium, that is to say a medium compatible with the tissues, mucosae, skin, nails and hair. Thus, the composition containing one or more substance P antagonists may be injected, swallowed or applied to the skin, in particular of the face, neck, hair, nails, major folds or any other area of the skin of the body, and the mucosae (buccal, jugal, gingival, genital, anal).

For a substance to be recognized as a substance P antagonist, it must satisfy the following characteristic:
have a pharmacological activity antagonistic to substance P, that is to say induce a coherent pharmacological response in at least one of the following two tests:
the antagonist substance must decrease the extravasation of plasma through the vascular wall induced by capsaicin or by an antidromic nervous stimulation, or alternatively
the antagonist substance must cause an inhibition of the smooth muscle contraction induced by the administration of substance P.

The substance P antagonist can, in addition, have a selective affinity for the tachykinin NK1 receptors.

The substance P antagonist of the invention may be functional or receptor-directed, that is to say may inhibit the synthesis and/or release of substance P, or prevent its binding and/or modulate its action.

The substance P antagonist of the invention can be, in particular, a peptide or a non-peptide derivative, and more specifically a compound containing a nitrogen, sulphur or oxygen heterocycle, or a compound comprising a nitrogen atom linked directly or indirectly to a benzene ring.

It is possible to use in the invention, for example, as a substance P antagonist peptide, sendide and spantide II.

Sendide corresponds to the formula:

in which:
Tyr represents tyrosine,
D-Phe represents D-phenylalanine,
Phe represents phenylalanine,
D-His represents D-histidine,
Leu represents leucine,
Met represents methionine.

Spantide II corresponds to the formula:

in which:

D-NicLys represents D-lysine nicotinate,

Pro represents proline,
3-Pal represents 3-pyridylalanine,
D-Cl$_2$Phe represents D-dichlorophenylalanine,
Asn represents asparagine,
D-Trp represents D-tryptophan,
Phe represents phenylalanine,
Leu represents leucine,
Nle represents norleucine.

It is also possible to use in the invention, as a substance P antagonist peptide, the peptides described in the documents U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569 and GB-A-2,216,529.

The non-peptide substance P antagonists which can be used in the invention are, in particular, compounds comprising a hetero atom linked directly or indirectly to a benzene ring or contained in a heterocycle. In particular, this hetero atom is an oxygen, nitrogen or sulphur atom.

As a heterocyclic compound containing a nitrogen atom, those described in the following documents may be used in the invention:
EP-A-360,390, EP-A-429,366, EP-A-430,771, EP-A-499,313,
EP-A-514,273, EP-A-514,274, EP-A-514,275, EP-A-514,276,
EP-A-520,555, EP-A-528,495, EP-A-532,456, EP-A-545,478,
EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116 and WO-A-94/08997.

In particular, the compound comprising at least one nitrogen heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

The compounds containing a sulphur or oxygen atom which can be used in the invention are, in particular, heterocyclic oxygen or sulphur compounds such as furan derivatives, benzofuran derivatives, thiophene derivatives and benzothiophene derivatives, optionally containing nitrogenous substituents, such as the heterocyclic compounds described in the documents U.S. Pat No. 4,931,459, U.S. Pat. No. 4,910,317 and EP-A-299,457, and more especially alkoxy- and/or aryloxytetrazolylbenzofurancarboxamides or alkoxy- and/or aryloxytetrazolylbenzothiophenecarboxamides.

As compounds containing a nitrogen atom linked directly or indirectly to a benzene ring, those described in the following documents may be mentioned: EP-A-522,808, WO-A-93/10073 and WO-A-93/01165. In particular, ethylenediamine derivatives such as N,N'-bis[bis(3,5-dimethylbenzyl)]ethylenediamine or N,N'-bis[bis(3,5-dimethoxybenzyl)]ethylenediamine may be mentioned. These compounds are described as reaction intermediates in the document WO-A-93/11338 filed in the name of the Applicant.

The substance P antagonists may be synthesized or extracted from natural products (plant or animal).

In the compositions of the invention, the substance P antagonist can preferably be used in an amount ranging from 0.000001 to 5% by weight relative to the total weight of the composition, and especially in an amount ranging from 0.0001 to 0.1% by weight relative to the total weight of the composition.

The compositions of the invention may be presented in all pharmaceutical dosage forms normally used, depending on whether the composition has to be swallowed, injected or applied to the skin or mucosae.

For topical application, the composition may take the form, in particular, of aqueous or oily solutions or of dispersions of the lotion or serum type, of emulsions of liquid or semi-liquid consistency of the milk type, obtained by dispersing a fatty phase in an aqueous phase (O/W) or vice versa (W/O), or of suspensions or emulsions of soft consistency of the cream or aqueous gel type or which are anhydrous, of microemulsions or alternatively of microcapsules or microparticles, or of vesicular dispersions of the ionic and/or nonionic type. These compositions are prepared according to the standard methods.

It may also be used for the scalp in the form of aqueous, alcoholic or aqueous-alcoholic solutions, or in the form of creams, Gels, emulsions or foams, or alternatively in the form of aerosol compositions also containing a propellent agent under pressure.

For injection, the composition may take the form of an aqueous or oily lotion or the form of a serum.

For swallowing, the composition may take the form of capsules, syrup, granules or tablets.

The amounts of the different constituents of the composition according to the invention are those traditionally used in the fields in question.

These compositions constitute, in particular, cleansing, protective, treatment or skin care creams for the face, hands, feet, major anatomical folds or body, protective or skin care body milks, or lotions, gels or foams for care of the skin or mucosae, such as cleansing or disinfecting lotions, bath compositions and compositions containing a bactericidal agent.

The compositions according to the invention can also consist of solid preparations constituting cleansing soaps or bars.

The compositions may also be packaged in the form of an aerosol composition also containing a propellent agent under pressure.

When the composition of the invention is an emulsion, the proportion of the fatty phase can range from 5% to 80% by weight, and preferably from 5% to 50% by weight, relative to the total weight of the composition. The oils, waxes, emulsifiers and coemulsifiers used in the composition in emulsion form are chosen from those traditionally used in the cosmetics field. The emulsifier and the coemulsifier are present in the composition in a proportion ranging from 0.3 to 30% by weight, and preferably from 0.5 to 20% by weight, relative to the total weight of the composition. The emulsion can, in addition, contain lipid vesicles.

When the composition is an oily gel or solution, the amount of oil can range up to more than 90% of the total weight of the composition.

In a known manner, the pharmaceutical or dermatological composition of the invention can also contain adjuvants which are customary in the fields in question, such as hydrophilic or lipophilic gelling agents, preservatives, antioxidants, solvents, perfumes, fillers, sunscreen agents, odour adsorbers and colouring matter. The amounts of these different adjuvants are those traditionally used in the cosmetics field, and are, for example, from 0.01% to 10% of the total weight of the composition. These adjuvants, depending on their nature, may be introduced into the fatty phase, into the aqueous phase and/or into lipid spherules.

As oils which can be used in the invention, mineral oils (liquid paraffin), vegetable oils (liquid fraction of shea butter, sunflower oil), animal oils (perhydrosqualene), synthetic oils (Purcellin oil), silicone oils or waxes (cyclomethicone) and fluorinated oils (perfluoro polyethers) may be mentioned. Fatty alcohols and fatty acids (stearic acid) may be added to these oils. Waxes such as beeswax and carnauba wax or paraffin may also be used.

As emulsifiers which can be used in the invention, glyceryl stearate, polysorbate 60 and the PEG-6/PEG-32/glycol stearate mixture sold under the name Tefose$^R$ 63 by the company Gattefosse may be mentioned as examples.

As solvents which can be used in the invention, lower alcohols, in particular ethanol and isopropanol, and propylene glycol may be mentioned.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminium stearates and hydrophobic silica may be mentioned.

It is, in addition, possible to introduce hydrophilic active agents such as proteins or protein hydrolysates, amino acids, polyols, urea, sugars and sugar derivatives, vitamins, starch, plant extracts (Aloe vera) and hydroxy acids (citric, lactic, glycolic, tartaric).

It is also possible to introduce lipophilic active agents such as retinol (vitamin A) and its derivatives, retinoids such as 13-cis- or all-trans-retinoic acid, tocopherol (vitamin E) and its derivatives, essential fatty acids, ceramides, essential oils and salicylic acid and its derivatives (5-n-octanoylsalicylic). Salicylic, lactic, acetic, and the like, acids act, in particular, as antiseptics.

The compositions which follow illustrate the invention: the proportions shown are percentages by weight.

Composition 1:
Disinfectant lotion for the face or mucosae

| | |
|---|---|
| N,N'-Bis[bis(3,5-dimethoxybenzyl)]ethylenediamine | 5.00 |
| Antioxidant | 0.05 |

-continued

| | |
|---|---|
| Isopropanol | 40.00 |
| Preservative | 0.30 |
| Water qs | 100% |

This composition may be used both for treating lichen planus or pigmentary lichens and for treating pruriginous toxicoderma.

Composition 2:
Face or body gel for the treatment of lichen planus

| | |
|---|---|
| N,N'-Bis[bis(3,50dimethoxybenzyl)]ethylenediamine | 0.05 |
| Hydroxypropylcellulose (Klucel H sold by the company Hercules) | 1.00 |
| Salicyclic acid | 1.00 |
| Antioxidant | 0.05 |
| Isopropanol | 40.00 |
| Preservative | 0.30 |
| Water qs | 100% |

Composition 3:
Cream (oil-in-water emulsion) for the treatment of severe pruritus

| | |
|---|---|
| N,N'-Bis[bis(3,5-dimethoxybenzyl)]ethylenediamine | 0.2 |
| Glyceryl stearate | 2.00 |
| Lactic acid/acetic acid | 1.00 |
| Polysorbate 60 (Tween 60 sold by the company ICI) | 1.00 |
| Stearic acid | 1.40 |
| Triethanolamine | 0.70 |
| Carbomer | 0.40 |
| Silicone oil | 12.00 |
| Perhydrosqualene | 12.00 |
| Antioxidant | 0.05 |
| Perfume | 0.5 |
| Preservative | 0.30 |
| Water qs | 100% |

Composition 4:
Gel for the treatment of lichens

| | |
|---|---|
| Sendine | 5.00 |
| Hydroxypropylcellulose (Klucel H) | 1.00 |
| Antioxidant | 0.05 |
| Isopropanol | 40.00 |
| Preservative | 0.30 |
| Water qs | 100% |

Composition 5:
Cream (oil-in-water emulsion) for anal

| | |
|---|---|
| Spantide II | 5.00 |
| Cetyldimethicone copolyol | 2.50 |
| NaCl | 0.60 |
| NaOH qs | pH 5 |
| Cyclomethicone | 18.00 |
| Polypropylene glycol myristyl ether containing 3 mol of propylene glycol | 6.00 |
| Glycerol | 3.00 |
| Preservative | 0.20 |
| Water qs | 100% |

Composition 6:
Cream (oil-in-water emulsion) for the treatment of severe pruritus This composition differs from Composition 3 by the presence of 0.05% of lidocaine instead of 1% of lactic/acetic acids.

We claim:

1. A method for treating a subject having a condition selected from the group consisting of lichens, prurigo, pruriginous toxicoderma and pruritus comprising treating said subject with an effective amount of a pharmaceutical or dermatological composition comprising at least one of the substance P antagonists sendide or spantide II.

2. The method of claim 1, wherein said pharmaceutical or dermatological composition is administered by a route selected from the group consisting of injection, oral, and topical administration.

3. The method according to claim 1, wherein the pharmaceutical or dermatological composition is topically applied to the skin or mucosae.

4. The method of claim 1, wherein the amount of the substance P antagonist in said composition ranges from 0.000001 to 5% by weight relative to the total weight of the composition.

5. The method of claim 1, wherein the amount of the substance P antagonist in said composition ranges from 0.0001 to 0.1% by weight relative to the total weight of the composition.

6. The method of claim 1, wherein the composition is selected from the group consisting of aqueous, oily, or aqueous-alcoholic solutions, water-in-oil emulsions, oil-in-water emulsions, microemulsions, aqueous gels, hydrous gels, serums, dispersions of vesicles, dispersions of microcapsules and dispersions of microparticles.

7. The method of claim 1, wherein the composition further comprises at least one active agent selected from the group consisting of proteins, protein hydrolysates, amino acids, polyols, urea, sugars, vitamins, starches, plant extracts, hydroxy acids, retinoids, essential fatty acids, ceramides, essential oils and salicylic acid.

8. The method of claim 1, wherein the composition further comprises at least one adjuvant selected from the group consisting of hydrophilic or lipophilic gelling agents, preservatives, anti-oxidants, solvents, perfumes, fillers, sunscreen agents, odor absorbers, and colorants.

9. The method of claim 8, wherein the amount of said adjuvant ranges from 0.01% to 10% relative to the total weight of the composition.

10. The method of claim 1, wherein the composition is an oily gel or solution.

11. The method of claim 7, wherein the oil is selected from the group consisting of mineral oils, vegetable oils, animal oils, synthetic oils, silicone oils, waxes, and fluorinated oils.

12. The method of claim 11, wherein the composition further comprises an emulsifier selected from the group consisting of glycerol stearate, polysorbate 60, and polyethyleneglycol/glycol stearate mixtures.

13. The method of claim 1, wherein the composition further comprises a lower alcohol solvent.

14. The method of claim 1, which is used for the treatment of lichens.

15. The method of claim 1, which is used for the treatment of prurigo.

16. The method of claim 1, which is used for the treatment of pruriginous toxicoderma.

17. The method of claim 1, which is used for the treatment of pruritus.

18. The method of claim 1, wherein said substance P antagonist exhibits at least one of the following properties:

(i) it decreases the extravasation of plasma through the vascular wall induced by capsaicin or by an antidromic nervous stimulation; or (ii) it causes an inhibition of smooth muscle contraction induced by substance P administration.

19. The method of claim 18, wherein said substance P antagonist further comprises a selective affinity for the tachykinin NK1 receptor.

* * * * *